US009057058B2

(12) United States Patent
Goel et al.

(10) Patent No.: US 9,057,058 B2
(45) Date of Patent: Jun. 16, 2015

(54) PROCESS FOR THE PREPARATION OF TALC BASED FORMULATION FOR LDPE-DEGRADING BACTERIAL CONSORTIA

(75) Inventors: Reeta Goel, Uttarakhand (IN); Aditi Sah, Uttarakhand (IN); Harshita Negi, Uttarakhand (IN); Anil Kapri, Uttarakhand (IN)

(73) Assignees: Department of Biotechnology Delhi, New Delhi (IN); G.B. Pant University of Agriculture and Technology, Pantnagar, Uttarakhand (IN)

( * ) Notice: Subject to any disclaimer, the term of this patent is extended or adjusted under 35 U.S.C. 154(b) by 396 days.

(21) Appl. No.: 13/284,034

(22) Filed: Oct. 28, 2011

(65) Prior Publication Data

US 2012/0196351 A1    Aug. 2, 2012

(30) Foreign Application Priority Data

Jan. 31, 2011    (IN) .............................. 213/DEL/2011

(51) Int. Cl.
*C12N 1/20*    (2006.01)
*C12N 1/04*    (2006.01)

(52) U.S. Cl.
CPC ... *C12N 1/20* (2013.01); *C12N 1/04* (2013.01)

(58) Field of Classification Search
None
See application file for complete search history.

(56) References Cited

U.S. PATENT DOCUMENTS 7,429,478 B2 *    9/2008    Kumar et al. .............. 435/252.4

OTHER PUBLICATIONS

Muis, A., Indonesian Journal of Agricultural Science, vol. 7 (2), 2006, pp. 51-56.*
Roy et al., Polymer Degradation and Stability 93 (2008) 1917-1922.*
Alok et al., J. Microbiol. Biotechnol. (2008), 18(3), 477-482.*
Meyer et al., "United States Department Of Agriculture-Agricultural Research Service research programs on microbes for management of plant parasitic nematodes," Pest Management Science, 2003, pp. 665-670, 59.
Trivedi et al., "Plant growth promotion abilities and formulation of *Bacillus megaterium* strain B 388 (MTCC6521) isolated from a temperate Himalayan location," Indian Journal of Microbiology, Sep. 2008, pp. 342-347, 48.
Trivedi et al., "Carrier-based preparations of plant growth-promoting bacterial inoculants suitable for use in cooler regions," World Journal of Microbiology & Biotechnology, 2005, pp. 941-945, 21.
Filho et al., "Stability and Persistence of Two Formulations Containing *Anticarsia gemmatalis* Nuclear Polyhedrovirus (AgMNPV)," Neotropica Entomology, Sep. 2001, pp. 411-416, 30(3).
Pandey et al., "Influence of Bacterial Inoculation on Maize in Upland Farming Systems of the Sikkim Himalaya," Soil Biology and Biochemistry, 1998, pp. 379-384, vol. 30, No. 3.
Brar et al., "Recent advances in downstream processing and formulations of *Bacillus thuringiensis* based biopesticides," Process Biochemistry, 2006, pp. 323-342, 41.
Tu et al., "Adjuvants. In: Weed Control Methods Handbook: Tools and Techniques for Use in Natural Areas," The Nature Conservancy, 2005, pp. 8.1-8.23, Chapter 8.
Sabaratnam et al., "Formulation of a Streptomyces Biocontrol Agent for the Suppression of Rhizoctonia Damping-off in Tomato Transplants," Biological Control, 2002, pp. 245-253, 23.
Arora et al., "Sawdust as a superior carrier for production of multipurpose bioinoculant using plant growth promoting rhizobial and pseudomonad strains and their impact on productivity of Trifolium repense," Current Science, Jul. 2008, pp. 90-94, vol. 95, No. 1.
Ting et al., "An in vitro Assessment on the Efficacy of Clay-Based Formulated Cells of Pseudomonas Isolate UTAR EPA2 for Petrol Degradation," American Journal of Applied Sciences, 2010, pp. 178-184, 7(2).
Orhan et al., "Enhancement of biodegradability of disposable polyethylene in controlled biological soil," International Biodeterioration & Biodegradation, 2000, pp. 49-55, 45.
Yamada-Onodera et al., "Degradation of polyethylene by a fungus, Penicillium simplicissimum YK, " Polymer Degradation and Stability, 2001, pp. 323-327, 72.
Hadad et al., "Biodegradation of polyethylene by the thermophilic bacterium Breevibacillus borstelensis," Journal of Applied Microbiology, 2005, pp. 1093-1100, 98.
Chiellini et al., "Biodegradation of thermally-oxidized, fragmented low-density polyethylenes," Polymer Degradation and Stability, 2003, pp. 341-351, 81.
El-Shafei et al., "Biodegradation of disposable polyethylene by fungi and Streptomyces species," Polymer Degradation and Stability, 1998, pp. 361-365, 62.
Gilan et al., "Colonization, biofilm formation and biodegradation of polyethylene by a strain of Rhodococcus ruber," Applied Microbiology and Biotechnology, 2004, pp. 97-104, 65.
Shah et al., "Biological degradation of plastics: A comprehensive review," Biotechnology Advances, 2008, pp. 246-265, 26.
Arutchelvi et al., "Biodegradation of polyethylene and polypropylene," Indian Journal of Biotechnology, Jan. 2008, pp. 9-22, vol. 7.
Goel et al., "Bacterial consortia for low-density polyethylene biodegradation," Patent application based on No. 561/DEL/2010A, Issue No. 37/2011, date of application Mar. 9, 2010, receipt date: Mar. 11, 2010, publication date Sep. 16, 2011, Applicants Department of Biotechnology (DBT); and G.B. Pant University of Agriculture & Technology, pp. 1-18.

(Continued)

*Primary Examiner* — Irene Marx
(74) *Attorney, Agent, or Firm* — The Webb Law Firm

(57) ABSTRACT

This invention is a process for the preparation of talc based formulation for LDPE-degrading bacterial consortia. The process comprises preparing an active consortium. The active consortium is divided into four parts in centrifuge tubes. The tubes are spun at 5000 rpm. A supernatant is decanted from the tubes. The tubes are vortexed. Talc is added to each tube. The tubes with talc are again vortexed for some time to produce a homogeneous mixture. The mixture is poured into glass dishes. The dishes are kept at room temperature as aseptically for drying.

9 Claims, 2 Drawing Sheets

(56) References Cited

OTHER PUBLICATIONS

Figure 1:
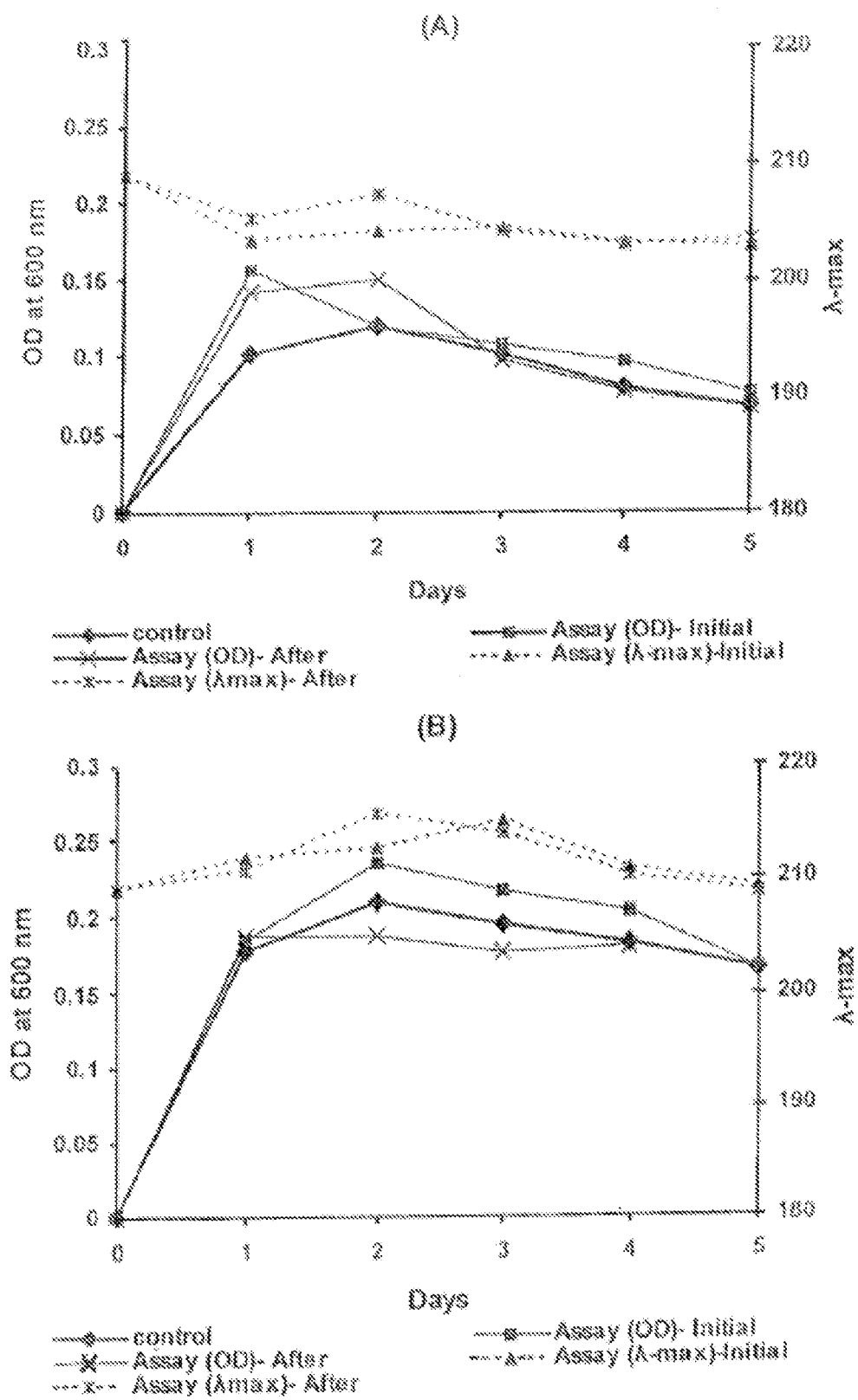

Soni et al., "Comparative Biodegradation Studies of Non-poronized and Poronized LDPE Using Indigenous Microbial Consortium," Journal of Polymer and The Environment, 2009, pp. 233-239, 17.

Soni et al., "Practical Applications of Rhizospheric Bacteria in Biodegradation of Polymers from Plastic Wastes," Plant-Bacteria Interactions, Strategies and Techniques to promote Plant Growth, 2008, pp. 235-243.

Negi et al., Comparative in-vitro biodegradation studies of epoxy and its silicone blend by selected microbial consortia, International Biodetereoration & Biodegradation, 2009, pp. 553-558, 63.

Kapri et al., "SPION-accelerated biodegradation of low-density polyethylene by indigenous microbial consortium," International Biodetereoration & Biodegradation, 2010, pp. 238-244, 64.

Sah et al., "Implications of Fullerene-60 upon in-vitro LDPE Biodegradation," Journal of Microbiology and Biotechnology, 2010, pp. 908-916, 20(5).

* cited by examiner

PROCESS FOR THE PREPARATION OF TALC BASED FORMULATION FOR LDPE-DEGRADING BACTERIAL CONSORTIA

FIELD OF THE INVENTION

This invention relates to a process for the preparation of talc based formulation for LDPE-degrading bacterial consortia.

BACKGROUND OF THE INVENTION

Carrier based formulation of microbial cells has long been established for applications in various fields like agriculture (Meyer, 2003; Trivedi and Anita Pandey, 2008; Trivedi et al., 2005), pharmaceutical (Tanaka et al 1993, Frokjaer and Hovgaard, 2000) and industrial (Tanaka et al., 1993) sectors. The aim of formulating viable cells to facilitate the delivery and handling processes and to ensure that adequate cell viability is sustained to increase the efficacy of the cells (Filho et al., 2001). Importance of native strains and ecological specificity while selecting the microbial inoculates for a specific environment is also realized (Pandey et al., 1998). For bioremediation purposes, formulated microbial cells are often applied using wet (liquid) formulations i.e by spraying inoculums suspensions on targeted sites, or using dry (solid) formulations where granules or dust are sprayed instead (Brar et al., 2006). The selection on the type of formulation developed and used is dependent on the nature of the active cells and factors related to the site of application such as application to aquatic or terrestrial landscapes, temperature, etc (Tu and Randall, 2005; Sabaratnam and Traquair, 2001). Most often, dry formulations are generally preferred over wet formulations because they provide extended shelf life and are easier to store and transport. In agriculture, various carriers have been used for the protection of bioinoculants such as alginate beads, charcoal, sand, sawdust and sugarcane bagasse, etc (Arora et al., 2008). Biodegradation of petrol by bacterial formulated with bentonite-based formulations has been reported by Ting et al, 2010. Plastic materials are widely used in industry, agriculture and day-to-day life. Because of their high durability, they accumulate in the environment at the rate of 25 million tons per year(Orhan and Buyukgungor, 2000). Thermoplastics are inert materials whose backbones consist of only long carbon chains. Their high hydrophobic level and high molecular weight characteristic structure makes them non-biodegradable. However, some microorganisms have been reported to utilize polyolefins with low molecular weight (Yamada-Onodera et al., 2001). The resistance of polyethylene to biodegradation stems for its high molecular weight, three-dimensional structure, and hydrophobic nature (Hadad et al, 2005) and lack of functional groups recognizable by existing microbial enzyme systems (Chiellini et al, 2003). Major strategies to facilitate PE disintegration and subsequent biodegradation, were focused on the direct incorporation of carbonyl groups within the backbone or on their in-situ generation by pre-oxidant additives like polyunsaturated compounds, transition metal ions and dithiocarbamates. These functional groups act as initiators of thermal and photo-oxidation of the hydrocarbon polymer chains (Chiellini et al, 2003), thereby increasing the surface hydrophilicity and facilitating biodegradation by micro-organisms. El-Shafei et. al (1998) investigated the ability of fungi and *Streptomyces* strains to attack degradable polyethylene bags containing 6% starch. Gilan et al., 2004 isolated a stain of *Rhodococus ruber* that could colonize & degrade PE. Fungal attachment has been reported on the surface of the LDPE pieces buried in soil mixed with sewage for 10 months, indicating possible utilization of plastic as a source of nutrient (Shah et al., 2008). The isolated fungal stains were identified as *Furasium* sp., *Aspergillus terreus* and *Penicillum* sp, respectively. In another study, two marine microorganisms viz. *Bacillus sphericus* and *Bacilius cereus* have also been recently reported for degradation of LDPE and HDPE (Sudhakar et al., 2008). Further a consortium of *Bacilius cereus, Bacilus pumilus* species and *Anthrobacter* sp was reported to degrade both LDPE as well as HDPE to an extent of nearly 22% within a period of two weeks (Satlewai et al., 2008). Similarly, a consortium of four different bacteria genara, Viz. *Bacterium* Te68R, *Bacillus cereus, Proteobacterium* Sp. and *Anthrobacter luteolus* has been reported to degrade non-poronized and poronized forms of LDPE (Soni et. al., 2009).

With a view of developing microbial inoculants for LDPE biodegradation, the described bacterial strains were isolated and have been reported earlier (Satlewel et al, 2008; Soni et al, 2008; Negi et al, 2009; Kapri et al, 2010 Sah et al, 2010; Kapri et al 2010) by our group.

OBJECTS OF THE INVENTION

An object of this invention is to propose a process for the preparation of talc based formulation for LDPE—degrading bacterial consortia.

Further objective of this invention is to propose a talc based formulation for determining shelf life of consortia during storage at ambient temperature.

Further object of this invention is to propose a talc based formulation for testing biodegradation efficiency and viability at regular intervals during storage.

BRIEF DESCRIPTION OF THE INVENTION

According to this invention there is provided process for the preparation of talc based formulation for LDPE-degrading bacterial consortia comprising the steps of:

preparing active consortium dividing the active consortium into four parts in centrifuge tubes spinning the tubes at 5000 rpm decanting the supernatant from the tubes subjecting the tubes to the step of vortexing, adding talc to each tube vortexing the tubes with talc again for some time to produce a homogeneous mixture, pouring the mixture into glass dishes keeping the plates at room temperature aseptically

BRIEF DESCRIPTION OF THE ACCOMPANYING DRAWINGS

FIG. 1 relates to comparative in vitro LDPE biodegradation assay of H (A) and consortium L (B) initially and after formulation, respectively.

Figure 2:
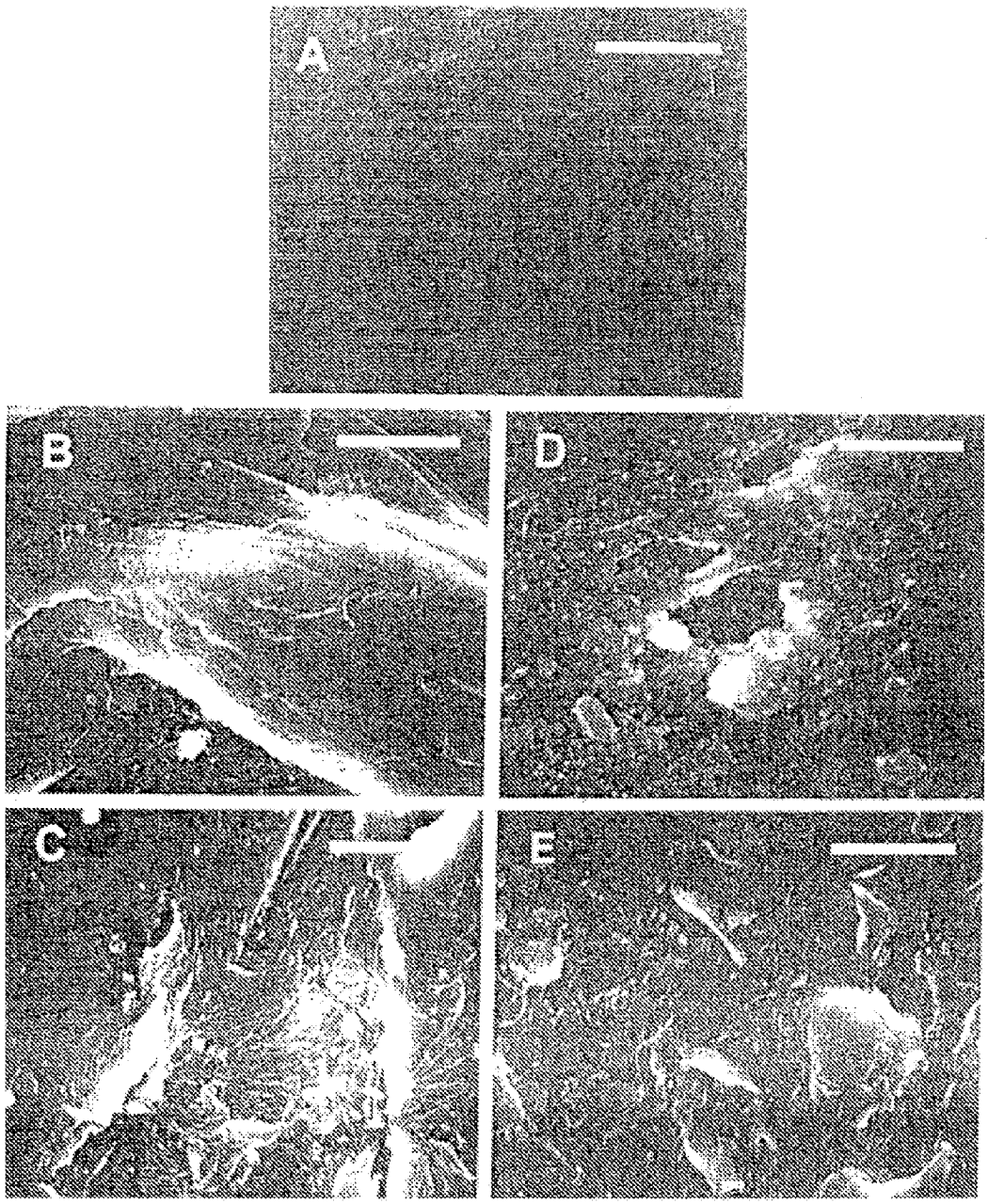

FIG. 2 relates to comparative SEM micrographs of LDPE film degraded by consortium H (B and C) and L(D and E) before and after formulation in talc, respectively, by taking pure LDPE film as control (A). Scale bars=10 µm; Magnification=3.00 KX.

DETAILED DESCRIPTION OF THE INVENTION

Talc

Talc was purchased from HiMedia Lab Pvt Ltd, Mumbai, India. It is composed of Talcum; steatite; Talc, fine powder and Hydrous magnesium silicate.

Bacterial Isolates

The bacterial cultures were obtained from departmental culture collection of Microbiology, CBSH, G.B. Pant University of Agriculture and Technology, Patnagar, India. The bacterial strains were characterized by 16S rDNA sequencing and identified by similarity scores returned by NCBI-BLAST. The sequences were submitted to NCBI GenBank. The culture was identified as *Microbacterium* sp. strain MK3 (DQ318884)(deposited on Mar. 2, 2012 as identification reference *Microbacterium* sp. (MK3) and Accession No. MCC0001 with the Microbial Culture Collection (MCC) at the National Centre for Cell Science (NCCS) in Pune University Campus, Ganeshkhind; Pune 411 007, Maharashtra, India), *Pseudomonas putida* strain MK4 (DQ318885) (deposited on Mar. 2, 2012 as identification reference MK4 and Accession No. MCC0002 with the Microbial Culture Collection (MCC) at the National Centre for Cell Science (NCCS) in Pune University Campus, Ganeshkhind; Pune 411 007, Maharashtra, India), *Bacterium* Te68R strain PN12 (DQ423487) (deposited on Mar. 2, 2012 as identification reference *Bacterium* Te68R (PN12) and Accession No. MCC0003 with the Microbial Culture Collection (MCC) at the National Centre for Cell Science (NCCS) in Pune University Campus, Ganeshkhind; Pune 411 007, Maharashtra, India), *Pseudomonas aeruginosa* strain PS1 (EU741797) (deposited on Mar. 16, 2012 as identification reference *Pseudomonas aeruginosa* (PS1) and Accession No. MCC0005 with the Microbial Culture Collection (MCC) at the National Centre for Cell Science (NCCS) in Pune University Campus, Ganeshkhind; Pune 411 007, Maharashtra, India), *P. putida* strain PW1 (EU741798) (deposited on Mar. 16, 2012 as identification reference *Pseudomonas putida* (PW1) and Accession No. MCC0006 with the Microbial Culture Collection (MCC) at the National Centre for Cell Science (NCCS) in Pune University Campus, Ganeshkhind; Pune 411 007, Maharashtra, India) and *P. aeruginosa* strain C1 (EU753182) (deposited on Mar. 16, 2012 as identification reference *Pseudomonas aeruginosa* (C1) and Accession No. MCC0004 with the Microbial Culture Collection (MCC) at the National Centre for Cell Science (NCCS) in Pune University Campus, Ganeshkhind; Pune 411 007, Maharashtra, India). Based on preliminary nutritional screening, these were developed into two different consortia in groups of three: consortium H comprising of MK3, MK4, and PN12 strains; and consortium L comprising of PS1, PW1 and C1 strains (Table 1) The medium used for consortium preparation was nutrient broth (HiMedia) containing gm per liter: 7.0 $K_{2H}PO_4$; 2.0 $KH_2PO_4$; 0.5 $Na_3C_6H_5O_7$; 0.1$(NH_4)_2$ $SO_4$ and 0.1mg $SO_{4.7}H_2O$ (Hi Media, Mumbai, India). An aliquot of 200 ml was withdrawn from glycerol stocks and the cultures were revived by inoculating into 5.0 ml Nutrient Broth (Hi Media, India) test tubes at their optimum pH (7±0.02) and temperature (37±1° C.), respectively.

TABLE 1

BACTERIAL STRAINS USED IN THIS STUD

| Bacterial Strains | Consortia |
|---|---|
| *Microbacterium* sp. strain MK3 (DQ318884), *Psudomonas putida* Strain MK4 (DQ318885), *Bacterium* Te 68R PN12 (DQ423487) | Consortium H |
| *Psudomonas aeruginosa* strain PS1 (EU741797), *P. Putida* strain PW 1 (Eu741798), *P. aeruginosa* strain C1 (EU753182) | Consortium L |

Active Consortium Preparation

A single colony form each strain bacterial strain was inoculated in 10 ml Nutrient Broth and incubated at optimum pH (7±0.02) and temperature (37±1° C.) for overnight (12 h) with continuous shaking (120 rpm) until an OD of 0.6 was attained at 600 nm [$OD_{600}$]. Absorbance was recorded by using UV-Vis Spectrophotometer (Perkin Elmer, Lambda 35). The individual strains of each consortium (H&L) were mixed at equal proportions of the order of $35 \times 10^5$ (H) and $2.0 \times 10^7$ (L) colony forming units respectively and added into 200 ml nutrient broth. The broth was incubated at 37° C. and 120 rpm till the stationary phase was over (Goel et al., 561/Del/2010).

Development of Talc Based Formulation

Active consortium (200 ml) was divided into four parts, 50 ml each in centrifuge tubes and spin at 5000 rpm for 10 min. Later supernatant was partially decanted and the tubes were vortexed for 15 min. Then, 2.5 gm talc was weighed and added to each tube with pellets under sterile conditions. With a sterile spatula, the mixture is then emptied into glass petriplates. The plates were kept at room temperature (28±1° C.) aseptically.

Enumeration of Shelf Life/Viability

The viability of bacterial isolates in the formulation was ascertained by serial dilution method. 50 mg of talc based formulation was dissolved in 1 ml of sterile distilled water in an eppendorf tube. Later, 10 µl of suspension was dissolve in 990 µl of sterilized distilled water. Likewise dilution plating of $10^{-6}$ and $10^{-7}$ was done for consortium H and L, respectively in nutrient agar medium. The plates were incubated at 37±1° C. and viability was checked initially after 2 and 4 days. Thereafter, the cfu/ml counts were determined after regular interval of 7 days for subsequent 3 weeks, followed by 15 days' interval till $70^{th}$ day. The above pattern was followed keeping in view the rapidity of changes in viable counts. The plate count was carried out in triplicates and the final cfu/ml were the average of the three readings.

TABLE 2

EUMERATION OF TOTAL VIABLE COUNT OF RESPECTIVE CONSORTIA UNDER FORMULATION

| Consortia | Dilution Factor | Cfu/ml* at subsequent time intervals (days) | | | | | | | |
|---|---|---|---|---|---|---|---|---|---|
| | | $2^{nd}$ | $4^{th}$ | $11^{th}$ | $18^{th}$ | $25^{th}$ | $40^{th}$ | $55^{th}$ | $70^{th}$ |
| Consortium H | $10^6$ | 279 ± 2 | 276 ± 2 | 271 ± 2 | 269 ± 2 | 267 ± 2 | 269 ± 2 | 269 ± 2 | 270 ± 2 |
| Consortium L | $10^7$ | 174 ± 2 | 174 ± 2 | 130 ± 2 | 127 ± 2 | 116 ± 2 | 77 ± 2 | 54 ± 2 | 32 ± 2 |

Testing of Biodegradation Efficiency

For the biodegradation assay, 100 ml Minimal broth Davis w/o dextrose (pH 7.0±0.2) was taken in 250 ml Erlenmeyer flasks containing four LDPE film coupons (1 square inch). The flasks were inoculated with 300 µl of active consortium and the assay was performed with respective positive (minimal broth+consortia) and negative (minimal broth+LDPE) controls. The flasks were incubated at 37° C. with continuous shaking (120 rpm) and recovered after the stationary growth phase of the consortium was over. (Satlewal et al; 2008, Kapri et al, 2010 a, b). Degraded LPDE films were further confirmed for biodegradation using SEM (Goel et al 561/Del/2010).

We claim:

1. A process for the preparation of a talc based formulation for a low-density polyethylene-degrading bacteria consortium comprising the steps of:

providing a consortium comprising at least three bacteria strains each independently chosen from *Microbacterium* sp. Strain MK3 (MCC Accession No. MCC0001), *Pseudomonas putida* strain MK4 (MCC Accession No. MCC0002), *Bacterium* Te68R strain PN12 (MCC Accession No. MCC0003), *Pseudomonas aeruginosa* strain PS1 (MCC Accession No. MCC0005), *P. putida* strain PW1 (MCC Accession No. MCC0006), and *P. aeruginosa* strain C1 (MCC Accession No. MCC0004), dividing the consortium into four parts in centrifuge tubes, centrifuging the tubes, thereby forming a supernatant, decanting the supernatant from the tubes, vortexing the tubes before adding talc, adding talc to each tube thereby forming talc-containing tubes, vortexing the talc-containing tubes for a sufficient time to produce a homogeneous mixture, pouring the mixture into a glass dish, and drying the glass dish at room temperature aseptically.

2. The process as claimed in claim 1, wherein the tubes are centrifuged at 5000 rpm for 10 minutes.

3. The process as claimed in claim 1, wherein the tubes are vortexed for 15 minutes before adding talc.

4. The process as claimed in claim 1, wherein the talc-containing tubes are vortexed for 15 minutes.

5. The process as claimed in claim 1, wherein the glass dish is dried at room temperature at 28±1° C. aseptically.

6. The process as claimed in claim 1, wherein the consortium is prepared by inoculating the at least three bacteria in a nutrient broth at an optimum temperature with continuous shaking, mixing the at least three bacteria strains in equal proportions, and adding the at least three bacteria into nutrient broth incubating the said broth to produce the consortium.

7. The process as claimed in claim 6, wherein the nutrient broth comprises a beef extract and a peptone.

8. The process as claimed in claim 1, wherein the at least three bacteria strains consist of *Microbacterium sp.* strain MK3 (MCC Accession No. MCC0001), *Pseudomonas putida* strain MK4 (MCC Accession No. MCC0002), and *Bacterium* Te68R strain PN12 (MCC Accession No. MCC0003).

9. The process as claimed in claim 1, wherein the at least three bacteria strains consist of *Pseudomonas aeruginosa* strain PS1 (MCC Accession No. MCC0005), *P. putida* strain PW1 (MCC Accession No. MCC0006) and *P. aeruginosa* strain C1 (MCC Accession No. MCC0004).

\* \* \* \* \*

UNITED STATES PATENT AND TRADEMARK OFFICE
CERTIFICATE OF CORRECTION

| | | |
|---|---|---|
| PATENT NO. | : 9,057,058 B2 | Page 1 of 1 |
| APPLICATION NO. | : 13/284034 | |
| DATED | : June 16, 2015 | |
| INVENTOR(S) | : Reeta Goel et al. | |

It is certified that error appears in the above-identified patent and that said Letters Patent is hereby corrected as shown below:

ON THE TITLE PAGE

ITEM 56

Column 2, OTHER PUBLICATIONS, Line 16, delete "repense,"" and insert -- repens," --

Column 2, OTHER PUBLICATIONS, Line 28, delete "Breevibacillus" and insert -- Brevibacillus --

Signed and Sealed this
Twenty-second Day of December, 2015

Michelle K. Lee
*Director of the United States Patent and Trademark Office*